US005324279A

United States Patent [19]
Lancaster et al.

[11] Patent Number: 5,324,279
[45] Date of Patent: Jun. 28, 1994

[54] DISPOSABLE DIAPER WITH REFASTENABLE MECHANICAL FASTENING SYSTEM

[75] Inventors: E. Peter Lancaster, Gig Harbor; Richard H. Young, Puyallup, both of Wash.

[73] Assignee: Paragon Trade Brands, Inc., Federal Way, Wash.

[21] Appl. No.: 918,279

[22] Filed: Jul. 22, 1992

Related U.S. Application Data

[63] Continuation of Ser. No. 677,606, Mar. 27, 1991, Pat. No. 5,269,776, which is a continuation of Ser. No. 328,493, Mar. 24, 1989, abandoned.

[51] Int. Cl.⁵ ............................................. A61F 13/15
[52] U.S. Cl. ................................. 604/391; 604/387; 604/386; 604/385.2; 24/578; 24/306; 24/442
[58] Field of Search ............ 604/386, 387, 391, 385.2; 24/578, 587, 588, 306, 442

[56] References Cited

U.S. PATENT DOCUMENTS

| | | |
|---|---|---|
| 2,141,105 | 8/1936 | Eller et al. . |
| 2,607,348 | 8/1952 | Rosenblatt . |
| 2,931,361 | 4/1960 | Sostrin . |
| 3,019,152 | 1/1962 | Jones . |
| 3,177,904 | 4/1965 | Siverson . |
| 3,345,709 | 10/1967 | Bearman . |
| 3,484,835 | 12/1969 | Trounstine et al. . |
| 3,534,780 | 10/1970 | Hockmeyer et al. . |
| 4,067,338 | 1/1978 | Van Vliet . |
| 4,068,665 | 1/1978 | Nelson . |
| 4,111,205 | 9/1978 | Nemeth . |
| 4,123,826 | 11/1978 | Tanaka . |
| 4,144,887 | 3/1979 | Milnamow . |
| 4,178,933 | 12/1979 | Nemeth . |
| 4,186,744 | 2/1980 | Ness . |
| 4,237,889 | 12/1980 | Gobran . |
| 4,345,597 | 8/1982 | Tritsch . |
| 4,369,786 | 1/1983 | Miller . |
| 4,395,215 | 7/1983 | Bishop . |
| 4,410,325 | 10/1983 | Lare . |
| 4,410,327 | 10/1983 | Baggaley . |
| 4,516,975 | 5/1985 | Mitchell . |

(List continued on next page.)

FOREIGN PATENT DOCUMENTS

| | | |
|---|---|---|
| 10962/88 | 1/1988 | Australia . |
| 0116740 | 8/1984 | European Pat. Off. . |
| 87105322.9 | 4/1987 | European Pat. Off. . |
| 2101627 | 7/1972 | Fed. Rep. of Germany . |
| 3113020-A1 | 11/1982 | Fed. Rep. of Germany . |
| 2116704 | 7/1972 | France . |
| 2135568 | 1/1984 | United Kingdom . |
| 2146230 | 4/1985 | United Kingdom . |
| 2162737 | 2/1986 | United Kingdom . |

*Primary Examiner*—Paul Prebilic
*Attorney, Agent, or Firm*—Klarquist, Sparkman, Campbell, Leigh & Whinston

[57] ABSTRACT

A disposable absorbent garment includes a moisture impervious outer layer, a nonwoven moisture pervious inner layer, an absorbent layer sandwiched and encased between the inner and outer layers, with the sandwiched layers having opposed first and second waist edges and two opposed side margins. The garment further includes a fastener or closure system comprising a pair of gripping strips or extensions from each of the side margins along the second waist edge, each gripping strip having a plurality of first resiliently deformable connectors integrally formed therein. The fastener system further includes a pair of targets located on the outer layer along the first waist edge adjacent each side margin, each target having a plurality of second connectors integrally formed thereon which are adapted to engage the first connectors of the gripping strips. The first and second connectors comprise interlocking means of the fastener system and include a plurality of interlockable projections and receptacles. The projections and receptacles may be circular or of any polygonal shape or they may comprise interlocking ridges and grooves. In one embodiment, each of the first connectors is a receptacle comprising a throat which extends through the gripping strip, and each of the second connectors comprise a projection which projects through and interlocks with a gripping strip throat.

11 Claims, 4 Drawing Sheets

U.S. PATENT DOCUMENTS

| | | |
|---|---|---|
| 4,537,591 | 8/1985 | Coates . |
| 4,555,244 | 11/1985 | Buell . |
| 4,578,071 | 3/1986 | Buell . |
| 4,601,694 | 7/1986 | Ausnit . |
| 4,645,501 | 2/1987 | Teed . |
| 4,655,761 | 4/1987 | Grube et al. . |
| 4,662,875 | 5/1987 | Hirotsu et al. . |
| 4,680,030 | 7/1987 | Coates et al. . |
| 4,681,581 | 7/1987 | Coates . |
| 4,701,170 | 10/1987 | Wilson et al. . |
| 4,701,176 | 10/1987 | Wilson et al. . |
| 4,701,179 | 10/1987 | Kellenberger et al. . |
| 4,704,117 | 11/1987 | Mitchell . |
| 4,714,096 | 12/1987 | Guay . |
| 4,726,807 | 2/1988 | Young et al. . |
| 4,743,242 | 5/1988 | Grube et al. . |
| 4,749,605 | 6/1988 | Berger . |
| 4,869,724 | 9/1989 | Scripps . |
| 4,892,598 | 1/1990 | Stevens et al. ............... 604/385.2 |
| 4,894,060 | 1/1990 | Nestegard . |
| 5,180,620 | 1/1993 | Mende ............................ 604/385.2 |
| 5,219,342 | 6/1993 | Hatch et al. ..................... 604/386 |
| 5,221,276 | 6/1993 | Battrell ............................. 604/391 |

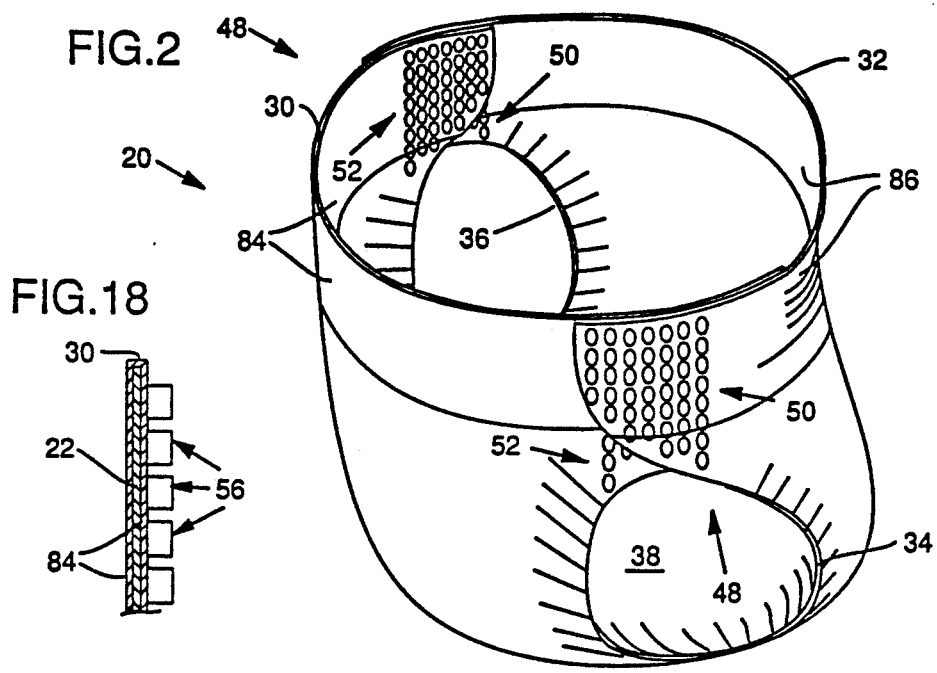
FIG. 2
FIG. 18
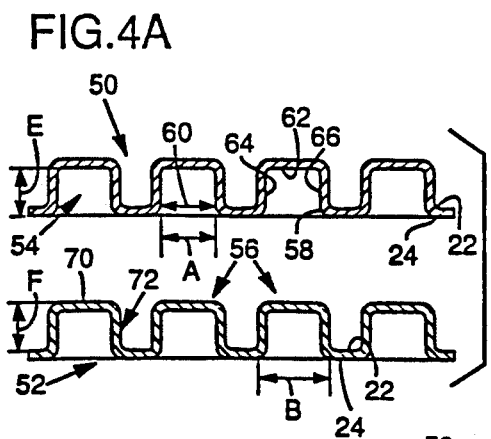
FIG. 4A
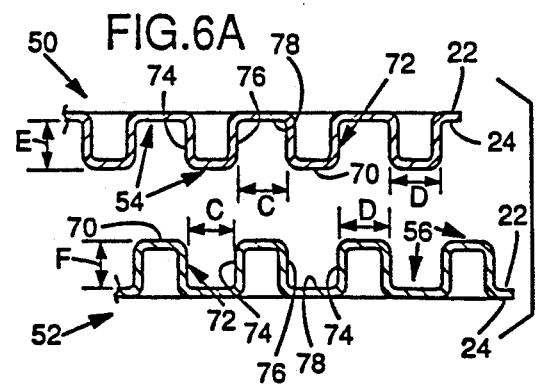
FIG. 6A
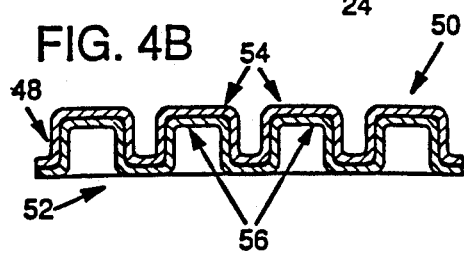
FIG. 4B
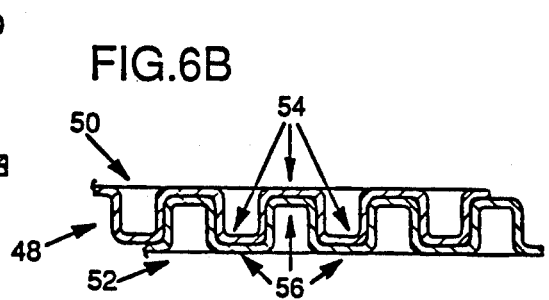
FIG. 6B

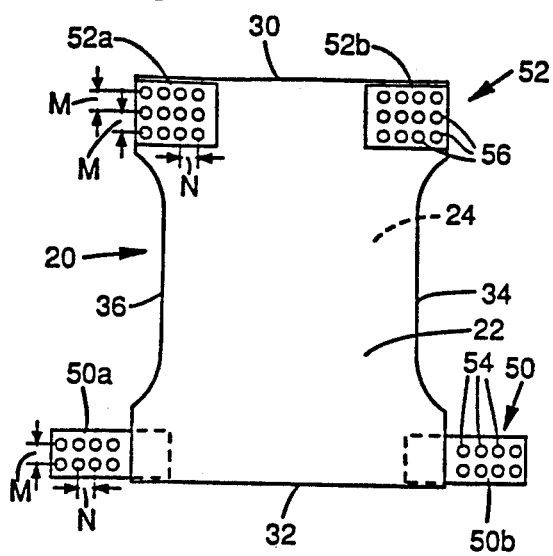
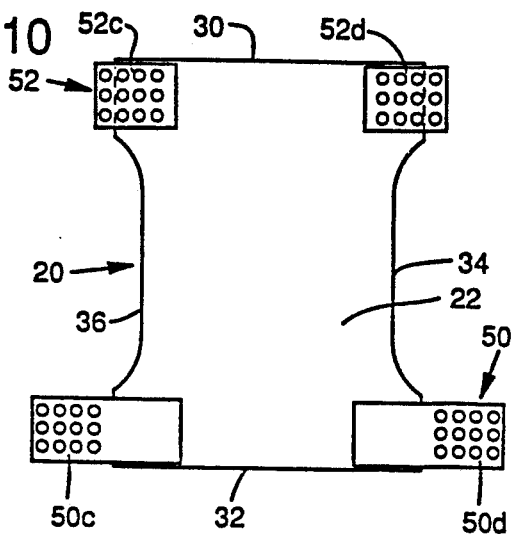
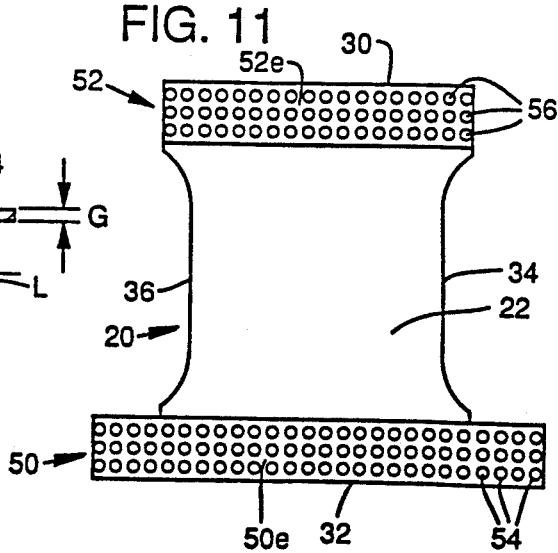
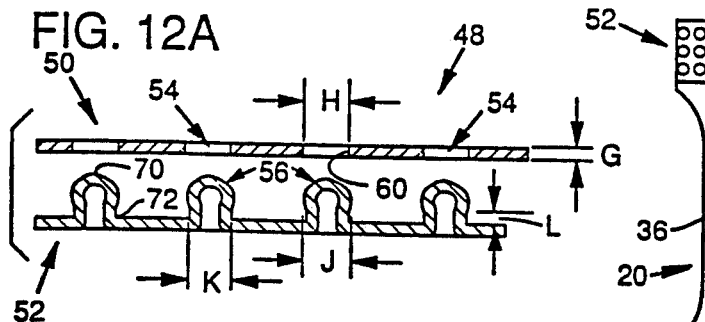
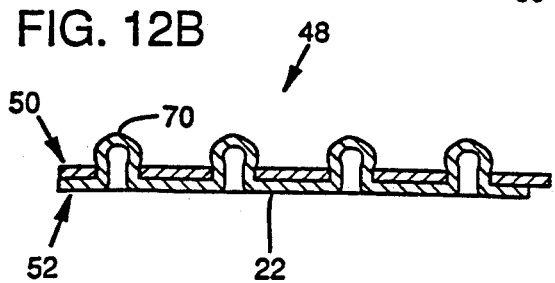

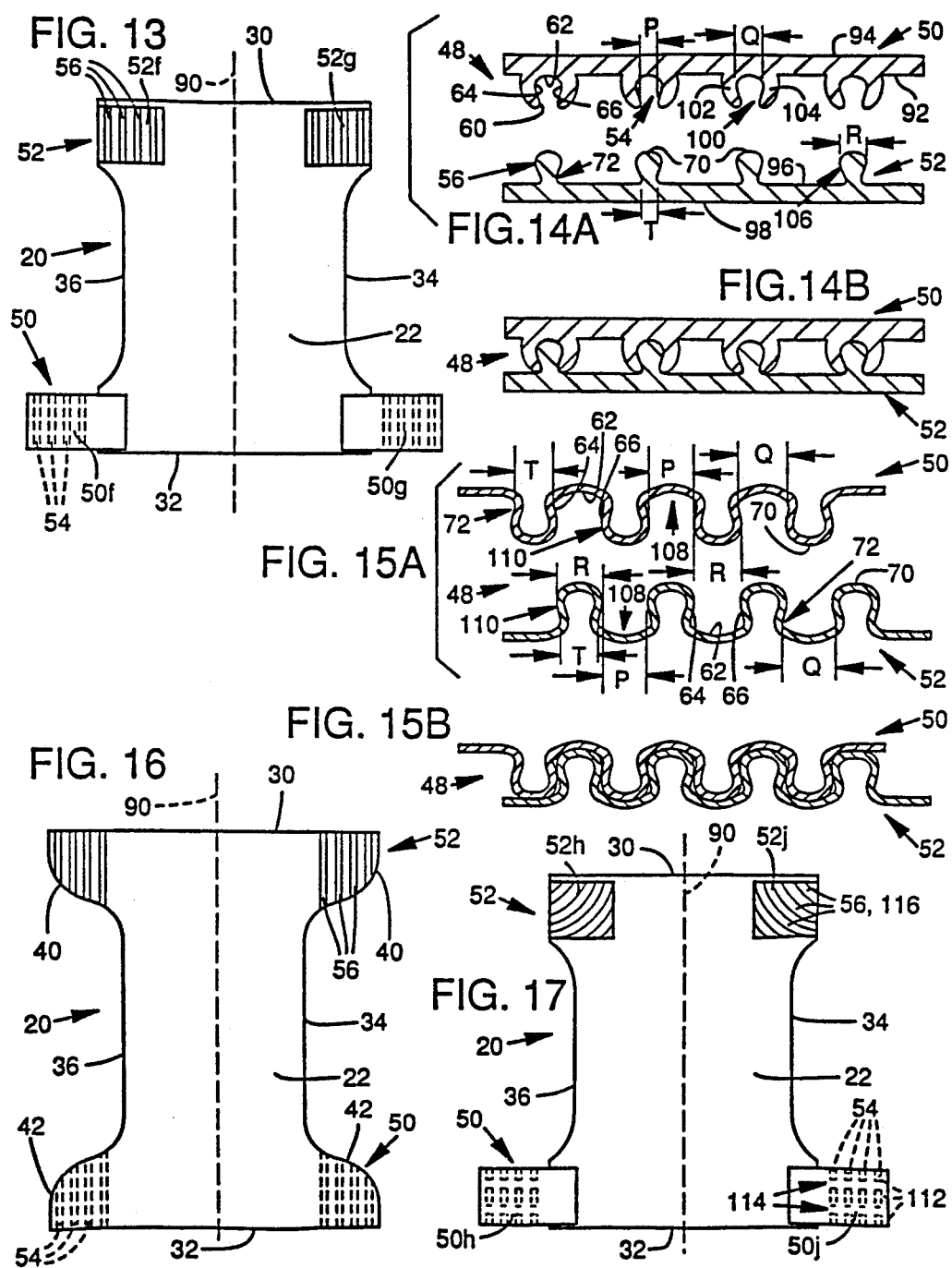

DISPOSABLE DIAPER WITH REFASTENABLE MECHANICAL FASTENING SYSTEM

This is a continuation of application Ser. No. 07/677,606 filed Mar. 27, 1991, U.S. No. 5,269,775 which is a continuation of U.S. patent application Ser. No. 07/328,493, filed Mar. 24, 1989, now abandoned.

BACKGROUND OF THE INVENTION

The present invention relates generally to a disposable absorbent garment, such as a diaper, and more specifically to an improved fastening system for securing the garment upon a wearer of the garment.

A variety of fasteners have been used on disposable diapers, reusable washable diapers, and waterproof garments, such as baby pants which are generally worn over the washable type of diaper. For example, U.S. Pat. No. 3,019,152 to Jones discloses baby pants having snap fasteners. U.S. Pat. No. 4,555,244 to Buell discloses a disposable diaper having reinforced holes through the diaper at the sides along the waistband. Buell provides a snap fastener which extends through the holes in the diaper to secure the diaper on a wearer. Such reusable snap fasteners inherently have a variety of small grooves and indentations which may entrap bodily wastes during wearing or changing of the diaper, leading to unsanitary conditions.

U.S. Pat. No. 2,931,361 discloses a cloth diaper having a triangular tongue portion which extends from the back waist of the diaper and which is adapted to be interwoven through vertical slots in a reinforcing piece along the front waist of the diaper. However, this interweaving is a time consuming process, and the connection is vulnerable to loosening during activity of the wearer.

A variety of refastenable adhesive tapes are used to secure a disposable absorbent garment, such as a diaper to a wearer, such as a baby. Typically, an adhesive tape is attached at each side along the back waist edge of the diaper. During the application and fitting of the diaper to the baby, typically the back waist edge is placed under a baby who is lying on his or her back. After suitably positioning the diaper under the baby, the front portion is brought up between the baby's legs and positioned along the lower front torso of the baby. The diaper is secured in place by releasing each adhesive tape from the inner side of the back waist and securing it on the outer surface along the front waist band. A suitable waist fitting is attained by varying the position of each tape along the front waist edge of the diaper.

While such adhesive tape fasteners offer convenience and safety over their traditional predecessor of cloth diapers with safety pin closures, the adhesive fasteners have several drawbacks. During the diapering of an active baby, the adhesive tapes or the areas along the front of the waist where the adhesive tapes are to attach may become coated with powders or ointments that are being applied to the baby. Such surface contaminations from ointments or powders severely degrade the quality of the adhesive closure, often rendering the diaper unusable.

While checking the diaper or during changing, the adhesive tape is susceptible to bending back upon itself and bonding with its own adhesive. Subsequent efforts to release the tape from itself often result in removing the adhesive from portions of the tape. This also degrades the tape for subsequent refitting on the baby or for disposal by rolling the waste within the diaper and using the tapes to secure the waste therein for disposal.

Disposable diapers suffer the disadvantage of liquid spreading by capillary action through the absorbent core. The liquid will migrate outwardly toward the waist and leg regions of the garment which may cause the undergarments of a wearer to become wet. Thus, a moisture barrier is desirable at the leg openings and waist. Such a moisture barrier is disclosed in U.S. Pat. No. 4,578,071 to Buell which discloses a diaper having a moisture barrier member bonded to a liquid impervious outer sheet. The outer sheet has a compacted portion with a multiplicity of spaced circles, dashes, ovals or gaps and spaces, arranged to provide a tortuous path for liquid to escape to the waist and leg openings. However, providing this tortuous moisture barrier path disadvantageously requires additional manufacturing steps and machinery, increasing the overall cost of the finished product.

Hood and loop fastener means, such as that sold under the trademark VELCRO, have been used on both disposable and reusable absorbent garments, such as diapers. Typically, VELCRO tabs extend from the back waistband and attach to matching VELCRO fasteners positioned along the front of the diaper. Such VELCRO closures have also been used in combination with D-ring belts to secure the waist portion of the garment. The D-ring belts are particularly useful in adult incontinence garments, where it is desirable to minimize bulk at the sides of the wearer.

An alternate type of VELCRO closure is disclosed in the Australian patent application No. AU-A-10962/88 to Scripps. The Scripps closure has mushroom-shaped hooks which are interconnectable with the traditional type of interwoven VELCRO loops.

The VELCRO fasteners also have disadvantages when applied to disposable diapers. A VELCRO fastener is typically a woven textile product which may be difficult and time consuming to apply to a disposable diaper, such as by sewing. The VELCRO fasteners are also more costly than adhesive fasteners, which also decreases their desirability for use on disposable garments. Additionally, the hooked portion of the VELCRO fastener may cause the wearer discomfort if the hook portion should inadvertently come in contact with the wearer's skin. Also, the woven textile backing material is often stiff and inflexible, and the edges or corners of the backing material may inadvertently rub against the wearer during use also causing discomfort. Additionally, during application of the garment the VELCRO hooks may snag other cloth in the area, such as clothing or a changing table cover, and become clogged with these foreign textile fibers. This clogging detracts from the integrity of the closure, and removing the foreign fibers is a time consuming task, which may also be painful if done by hand.

The related U.S. Pat. Nos. 4,701,170 and 4,701,176, both to Wilson, et al. and U.S. Pat. No. 4,701,179 to Kellenberger, et al., disclose another fixed position fastener system. A first pair of fastener members is attached along each side of the back waist for interconnection with a second pair of fastener members attached along each side of the front waist. Each fastener member has two fingers which extend along the surface of the diaper toward the transverse axis of the diaper. The fingers of the first pair of fasteners are adapted for interconnection with the fingers of the second pair of fasteners. To interconnect the fasteners, the garment is pulled tighter than in actual use to allow the fingers of the mating fasteners to intermesh and slide together to maintain the connection. Similarly, upon removal the garment must again be drawn tight to allow the fingers to slidably disengage. These fastener members are attached to the outer surface of the diaper with autogenous bonds, adhesives, or by stapling, riveting or sewing. The fastener members are of a plastic material having specific material properties, such as modulus of elasticity.

The fastener system of the Wilson, et al. and Kellenberger, et al. patents suffers from several disadvantages. The most notable of these disadvantages is the lack of adjustability of the fastener system to accommodate wearers of different sizes, or to allow tightening or loosening of the diaper during use. Additionally, the thickness of the interconnected fingers, adds to the bulk at the sides of the wearer. Since the fastener is of a rigid plastic it may be a source of discomfort when the wearer bends or twists at the waist. Additionally, upward leg movement at the hip joint may cause the fastener to dig into the waist and abdominal regions of the wearer further causing discomfort. Additionally, such fasteners may have sharp needle-like or knife-like edges resulting from flash, which is excess plastic that has escaped into the small space between mating plastic die halves. Such sharp edges can poke or actually cut the wearer or person applying the diaper to the wearer.

Thus, the need exists for an improved fastening system for a disposable absorbent garment, suitable for use on adults or babies or persons of ages therebetween, which is not susceptible to the above limitations and disadvantages.

SUMMARY OF THE INVENTION

It is an overall object of the present invention to provide an improved disposable absorbent garment and an improved closure or fastener system for such garments.

It is a further object of the present invention to provide a disposable absorbent garment which is economical to manufacture.

An additional object of the present invention is to provide a disposable absorbent garment having a fastening or closure system which is not degraded by surface contamination from ointments and powders which are often applied to the wearer of the garment prior to application of the garment.

Still a further object of the present invention is to provide a disposable absorbent garment having a closure system which is easily unfastened and refastenable when desired, yet which maintains closure of the garment during periods of wearer activity.

Another object of the present invention is to provide a disposable absorbent garment capable of being loosened or tightened when desired during wear.

Still another object of the present invention is to provide a disposable absorbent garment having fasteners which do not cause undue discomfort to the wearer of the garment.

An additional object of the present invention is to provide a disposable absorbent garment which does not leak around the waist edges, and which thereby prevents the escaping of moisture to the outer garments of a wearer.

Still another object of the present invention is to provide a disposable absorbent garment which does not unduly stretch out of shape along the waistband during wear.

Yet an additional object of the present invention is to provide an improved closure system suitable for baby diapers and adult incontinence briefs.

A further object of the present invention is to provide a closure system for a disposable absorbent garment which has a strong sheer strength and is relatively easy to peel off when desired.

An additional object of the present invention is to provide a closure system for a disposable absorbent garment which is not vulnerable to surface contamination from ointments, powders, textile fibbers and the like.

Still a further object of the present invention is to provide a closure system for a disposable absorbent garment which is not subject to inadvertent pull-out or breakage away from the balance of the garment.

According to one aspect of the present invention, a disposable absorbent garment is provided including a moisture impervious outer layer or sheet, a nonwoven moisture pervious inner layer or sheet, and an absorbent layer sandwiched and encased between the inner and outer layers. The sandwiched layers have opposed first and second waist edges and two opposed side margins. Fastening means are provided for securing the garment on a wearer of the garment. The fastening means includes gripping means extending from each of the side margins along the second waist edge and having a plurality of first resiliently deformable connectors integrally formed therein. The fastener means further includes target means located on the outer layer along the first waist edge for engaging and securing the gripping means. The target means have a plurality of second connectors integrally formed thereon which are adapted to engage the first connectors of the gripping means. The second connectors project outwardly from the outer layer and are adapted each to receive a first connector by pressing the first connectors substantially perpendicularly toward the outer layer to interengage the first and second connectors. The first and second connectors are sized such that upon interengagement the first connectors are deformed, and the first and second connectors resiliently grip one another to maintain the interconnection.

In an illustrated embodiment, the gripping means is a strip of a first thickness, and each of the first connectors of the gripping means comprises a throat having a first cross-sectional dimension. The throat of each of the first connectors extends through the gripping means strip and has a substantially circular cross section. In this embodiment, each of the second connectors of the target means includes a projection having a substantially circular cross section, a distal end portion and a middle portion spaced inwardly from the distal end portion. The distal end portion has a cross-sectional dimension slightly larger than the first cross-sectional dimension of the gripping means throat. The middle portion has a cross-sectional dimension substantially equal to the throat first cross-sectional dimension. The length of the middle portion of each of the second connector projections is substantially equal to the first thickness of the gripping means strip. In this manner, when the target means and the gripping means are coupled together, the distal end portion of the target means is positioned beyond the throat portion of the gripping means releasably to secure the garment upon the wearer.

In another illustrated embodiment, first and second moisture barrier strips are provided along the respective first and second waist edges of the garment. The first and second moisture barrier strips are each of a liquid impervious and embossable material. The gripping means connectors are embossed upon the second moisture barrier strip, and the target means connectors are embossed upon the first moisture barrier strip. In another embodiment, the gripping means and the target means are adhesively attached along the respective second and first waist edges.

In another illustrated embodiment, the first and second connectors of the respective gripping means and target means comprise interlocking ridges and grooves. The first connectors comprise a plurality of substantially parallel grooves formed in the gripping means. The target means second connectors comprise a plurality of substantially parallel grooves formed thereon and adapted for interconnection with the grooves of the gripping means.

According to another aspect of the present invention, a closure system is provided for a disposable garment. The closure system comprises gripping means extending from the second waist edge laterally of each of the side margins, and target means located on the outer layer along the first waist edge for engaging and securing the gripping means. The closure system further includes interlocking means integrally formed on the gripping means and the target means comprising a plurality of interlockable projections and receptacles for releasably interconnecting the gripping means with the target means.

According to another aspect of the present invention, a disposable garment is provided having the encasing inner and outer sheets joined along an outer boundary. The garment further includes fastener means comprising gripping means adjacent each side margin along the second waist edge of the garment. The fastener means further includes target means adjacent each side edge along the first waist edge of the garment. The gripping means and the target means are each of a resilient material. The fastener means also include interlocking means integrally formed on the gripping means and the target means for interconnecting the gripping means with the target means. The interlocking means comprises a plurality of interlockable projections and receptacles.

In an illustrated embodiment of the last mentioned aspect, the projections are substantially circular and arranged in rows and columns on the gripping means and the target means. The target means and gripping means are at least partially located in the outer boundary of the garment. The projections and receptacles are formed by deformation of the inner sheet and outer sheet at the locations of the target means and the gripping means. In one embodiment, each of the projections project outwardly from the outer sheet, with the deformation forming a receptacle which is recessed inwardly from the inner sheet and corresponds to one of the projections. Each receptacle has a first cross-sectional dimension. Each projection has a cross-sectional dimension slightly greater than the first cross-sectional dimension and which substantially coincides with the first cross-sectional dimension of an interengaged receptacle upon interengagement.

In another embodiment, the target means have projections which project outwardly from the outer sheet, and the gripping means have projections which project outwardly from the inner sheet. The projections on each of the target means and the gripping means are arranged in substantially parallel rows, with the rows on the target means alignable with the rows on the gripping means when the garment is worn. Each projection has at least two opposed walls substantially perpendicular to the sheet from which the projection projects. The receptacles of the interlocking means lie between adjacent projections and are bordered by one of the opposed walls of each adjacent projection. The projections are spaced such that each receptacle has a first cross-sectional dimension between the bordering walls of the adjacent projections. Each projection has a cross-sectional dimension at the opposed sidewalls that is slightly larger than the receptacle first cross-sectional dimension. In this manner, upon interengagement of the target means and the gripping means, the projections resiliently interlock with the receptacles to secure the garment on a wearer.

These and other objects, features and advantages of the present invention will become apparent to those skilled in the art from the following description and drawings.

BRIEF DESCRIPTION OF THE DRAWINGS

FIG. 2 illustrates a disposable absorbent garment according to FIG. 1 as it would be applied to a wearer of the garment;

FIGS. 4A and 4B are enlarged detailed views of the closure system illustrated in FIG. 3, with FIG. 4A illustrating the connectors of the system prior to engagement, and FIG. 4B illustrating the connectors of the system after engagement;

FIGS. 6A and 6B are enlarged detailed views of the closure system illustrated in FIG. 5, with FIG. 6A illustrating the connectors of the system prior to engagement, and FIG. 6B illustrating the connectors of the system after engagement;

FIGS. 9, 10 and 11 are top plan views illustrating three additional forms of a disposable absorbent garment of the present invention, each having an alternate embodiment of the closure system of the present invention;

FIGS. 12A and 12B are enlarged detailed views of the closure system illustrated in FIGS. 9, 10 and 11, with FIG. 12A illustrating the connectors of the system prior to engagement, and FIG. 12B illustrating the connectors of the system after engagement;

FIG. 13 is a plan view of one form of a disposable absorbent garment of the present invention;

FIGS. 14A and 14B are enlarged detailed views of the closure system illustrated in FIG. 13, with FIG. 14A illustrating the connectors of the system prior to engagement, and FIG. 14B illustrating the connectors of the system after engagement;

FIGS. 15A and 15B are alternate forms of the closure system illustrated in FIG. 13, with FIG. 15A illustrating the connectors of the system prior to engagement, and FIG. 15B illustrating the connectors of the system after engagement;

FIG. 16 is a plan view of one form of a disposable absorbent garment of the present invention, which may be manufactured according to the method illustrated in FIGS. 7 and 8;

FIG. 17 is a plan view of another form of a disposable absorbent garment of the present invention; and FIG. 18 is an enlarged cross-sectional view taken along line 18—18 of FIG. 8.

DETAILED DESCRIPTION

Figure 1:
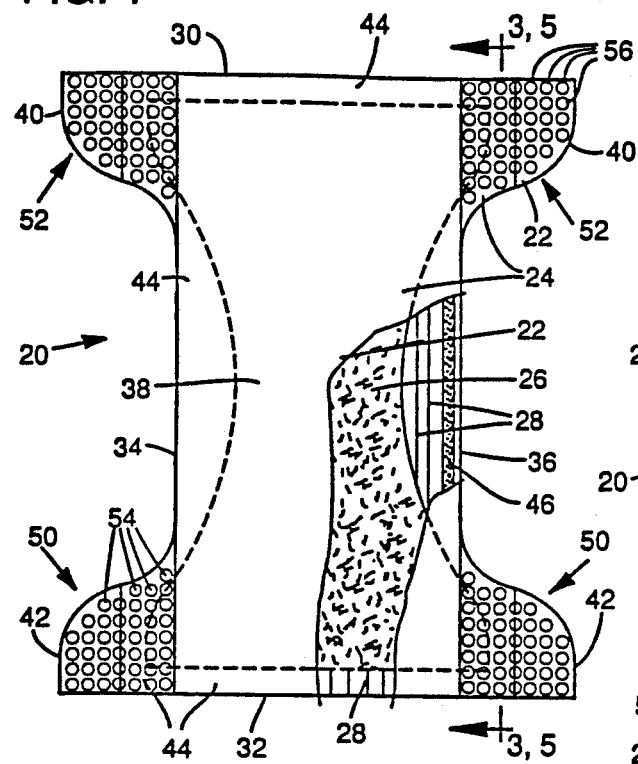
FIG. 1 is a cutaway plan view of one form of a disposable absorbent garment of the present invention.

FIG. 1 illustrates an embodiment of a disposable absorbent garment 20 manufactured in accordance with the invention having a moisture impervious outer layer or sheet 22, often referred to as a backsheet, and a moisture pervious nonwoven body-contacting inner layer or sheet 24, often referred to as a top sheet. A moisture absorbent fluff filler pad layer or core 26 is sandwiched and encased between the inner sheet 24 and the outer sheet 22. The encasement of the garment may be accomplished by bonding the layers together by a plurality of fine hot melt adhesive lines 28.

The disposable absorbent garment 20 is typically used as a baby or infant diaper or as an adult incontinence brief. The manufacture of such a garment is well-known in the art. One garment and method of manufacture is illustrated in U.S. Pat. No. 4,726,807 to Richard H. Young and Peter Lancaster, also coinventors of the present invention, which is herein incorporated by reference to illustrate the typical materials used and methods of manufacturing such garments.

For example, the moisture impervious outer layer 22 may be of a thin thermoplastic material, such as a pigmented polyethylene film having a thickness in the range of 0.02–0.04 mm. The moisture permeable inner sheet may typically be of a carded polyester fiber with a latex binder or of a spun-bonded polypropylene having continuous fibers and thermally bonded by patterned calendar rolls. The moisture absorbent layer or core 26 may be of wood fibers or other fibers such as chemical wood pulp, or any other suitable liquid absorbing material such as commercially available fluff pulp or of a fluffed bleached kraft softwood pulp. The hot melt adhesive lines 28 may be of the flexible rapid setting variety, such as those formulated from ethylene-vinyl acetate resins used with tackifiers and other additives.

The garment or diaper 20 also has a first waist edge 30, which may lie along the front waist of a wearer, and an opposed second edge 32, which may lie along the waist at the wearer's back. Two opposed side margins 34 and 36 define leg encircling openings when the garment is fitted on a wearer (see FIG. 2). Thus, with the first waist edge 30 to the front of a wearer, side margin 34 is the left leg side margin and side margin 36 is the right leg side margin. Lying between the opposed side margins 34, 36 is a crotch portion 38 which is central to the garment.

As shown in the embodiment of FIG. 1, the outer impervious layer 22 may extend outwardly from each of the opposed side margins 34, 36 along the first and second waist edges 30, 32. In this manner, a pair of first waist extensions 40 are formed extending from each side margin along the first waist edge 30. A pair of second waist extensions 42 are formed extending from each side margin along the second waist edge 32. The inner layer 24 may extend partially or completely over the waist extensions 40, 42 or it may terminate just beyond the outer boundary of the absorbent core 26 along an outer boundary 44. The outer boundary 44 defines the region in which the inner sheet 24 is bonded or joined to the outer sheet 22 to encase the absorbent core 26.

Thus, the sandwiched layers of the garment 20 as illustrated in FIG. 1, generally have an hourglass shape. The top and bottom of the hourglass shape form first and second waist portions of the garment, with the first waist portion comprising each of the first waist extensions 40 and the area of the diaper therebetween. The second waist portion comprises the second waist extensions 42 and the region of the garment along the second waist edge 32 between extensions 42. The opposed sides of the hourglass shape form the opposed side margins 34, 36. The crotch portion of the garment 38 is central to the hourglass shape, and has a narrower width than the waist portions.

In FIG. 2, showing the garment 20 as if fitted on a wearer, the side margins 34 and 36 are gathered and elasticized to create a better fitting garment which is more capable of retaining bodily wastes. There are a variety of methods for providing elasticized leg openings, and one such method is illustrated in U.S. Pat. No. 4,726,807, incorporated by reference above. Longitudinal ribbons 46 of a heat shrinkable polymeric material are placed along each of the opposed side margins 34, 36 during manufacture, and held in place by the fine hot melt adhesive lines 28. FIG. 1 illustrates the garment before heat has been applied to the ribbons 46, which will cause it to form the shirred or wrinkled edge with the accompanying transverse folds as shown in FIG. 2. If an elasticized waist portion with waist gathers are also desired, additional heat shrinkable ribbons 46 may be placed in the boundary area 44 adjacent the first and second waist edges 30 and 32. For clarity, the balance of the figures are shown without waist and leg gathers.

This invention features a new and improved closure or fastener system 48 for securing the garment 20 on a wearer of the garment and which includes gripping means 50, preferably of a resilient material, located along the second waist edge 32 and target means 52, preferably of a resilient material, located along the first waist edge 30 for engaging and securing the gripping means 50. The gripping means 50 are adjacent each side margin 34, 36, and may extend laterally from each side margin along the second waist edge 32. The target means 52 are illustrated as located on the outer layer 22 adjacent each side margin 34, 36. The fastener system 48 further includes interlocking means integrally formed on the gripping means 50 and the target means 52 for interconnecting the gripping means with the target means. To interlock the fastener system 48, the gripping means 50 and target means 52 overlap and interengage along the waist of a wearer, either at the sides or to the front of the wearer.

Several illustrated embodiments of the closure system 48 of the present invention are discussed in greater detail below. Each is capable of releasable and refastenable interconnection, and each is adjustable to fit varying sizes of wearer's waists.

The illustrated interlocking means includes a plurality of interlocking connectors, such as, interengaging projections and receptacles therefor. For example, referring to FIG. 1, the gripping means 50, which is preferably of a resilient and deformable material, is deformed to integrally define therein a plurality of first connectors 54. The target means 52 may also be of a resilient and deformable material, deformed to integrally define thereon a plurality of second connectors 56. In accordance with the specific illustrated embodiments of the invention shown herein, each second connector 56 is adapted to receive and engage a first connector 54 by pressing the gripping means 50 in a substantially perpendicular direction toward the outer layer 22 at the location of the target means 52. The first and second connectors 54, 56 are sized such that upon interengagement, one or both of the connectors are deformed, and resiliently grip one another to maintain this interconnection.

The first and second connectors 54, 56 are illustrated in FIG. 1 as having a substantially circular cross-sectional shape. However, other shapes of interlocking connectors would be equally suitable, such as rectangles, triangles, hexagons, or other polygonal shapes or combinations thereof, in addition to the embodiments described further below. Each of the first and second connectors 54, 56 are illustrated in an arrangement of rows and columns on the respective gripping means 50 and target means 52. The rows have substantially equal spacings between adjacent rows and the columns have substantially equal spacing between adjacent columns. The first connector rows and columns on the gripping means 50 are arranged to be alignable with the second connector rows and columns on the target means 52 for interengagement, as shown in FIG. 2. Other spacings and arrangements of the connectors 54, 56 may also be used, provided that such arrangements are alignable for interengagement of the closure system 48.

Figure 3:
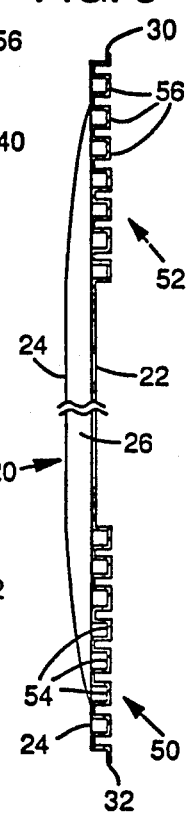
FIG. 3 is a cross section taken along line 3—3 of FIG. 1, showing the details of one form of the closure system of the present invention.

In the illustrated embodiment of FIGS. 3, 4A and 4B, each of the gripping means first connectors 54 comprise a receptacle recessed inwardly from the inner layer 24, and each of the target means second connectors 56 comprise a projection projecting outwardly from the outer sheet 22. Each of the first connector receptacles 54 comprises an entrance 58 which defines throat 60 having a first cross-sectional dimension A as shown in FIG. 4A. FIG. 4A illustrates the closure system 48 of this embodiment disconnected, whereas FIG. 4B illustrates the gripping means interengaged with the target means. Each receptacle further includes a bottom surface 62 and at least two opposed walls 64, 66 which extend between the entrance 58 and the bottom surface 62. In an alternate embodiment (not shown), the opposed sidewalls 64 and 66 may taper outward slightly so that at the widest point, the interwall cross-sectional dimension is greater than the first cross-sectional dimension A of throat 60.

Each of the second connector projections 56 comprise a distal end portion 70 and a middle portion 72 which is spaced inwardly from the distal end portion 70. In this embodiment, the first and second connectors 54, 56 are substantially the same size and shape.

Each first connector projection 56 has an outer or second cross-sectional dimension B which is slightly larger than the first cross-sectional dimension A and a second connector throat 60. Upon interconnection of the first and second connectors 54, 56, each of the illustrated first connector receptacles 54 deforms by expansion to admit a second connector projection 56. Thereafter, each receptacle throat 60 contracts resiliently to grip an admitted projection, thereby securing the interconnection. Additionally, each of the second connector projections 56 may deform by contraction to aid the interengagement, and then resiliently expand to maintain the interconnection. In this manner, upon engagement of each of the receptacles and projections of connectors 54, 56, the first and second cross-sectional dimensions A and B substantially coincide.

Figure 5:
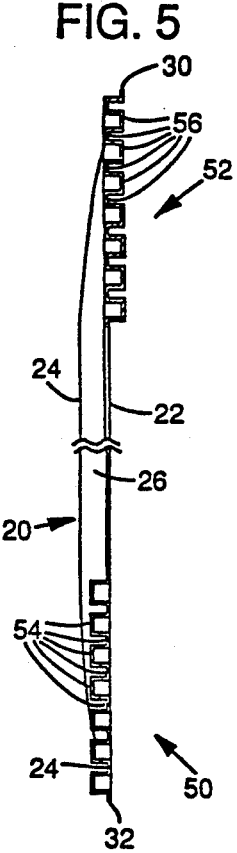
FIG. 5 is a cross section taken along line 5—5 of FIG. 1, showing the details of an alternate form of the closure system of the present invention.

Referring to the illustrated embodiment of FIGS. 5, 6A and 6B, each of the projections of the target means 52 project outwardly from the outer layer 22, as in the embodiment illustrated in FIGS. 3, 4A and 4B. However, each of the first connectors 54 of the gripping means 50 comprises a projection projecting outwardly from the inner layer 24, as shown in FIG. 5. In this embodiment, the projections of both the gripping means 50 and the target means 52 have a size and spacing which produces receptacles between the projections, such that the projections and receptacles of both the target means and gripping means interlock. Thus, the gripping means first connectors 54 comprise a plurality of spaced-apart projections having receptacles formed therebetween, the projections and receptacles both being located on the inner layer 24. The target means second connectors 56 similarly comprise a plurality of spaced-apart projections with receptacles formed therebetween and located on the outer layer 22. The projections on each target means 50 and each gripping means 52 are arranged in substantially parallel rows, with the rows on the target means 52 alignable with the rows on the gripping means 50 when the garment is worn.

As illustrated in FIG. 6A, each projection has a distal end 70 and at least two opposed sidewalls 74, 76 which are substantially perpendicular to the sheet from which the projections project. The receptacles lie between adjacent projections and have a bottom surface 78. Each receptacle has a first cross-sectional dimension C between the bordering walls 76, 74 of the adjacent projections. Each of the projections has a cross-sectional dimension D between the bordering walls 74, 76 thereof. The projection cross-sectional dimension D is slightly larger than the receptacle first cross-sectional dimension C. Thus, upon interengagement of the target means 52 and the gripping means 50, as shown in FIG. 6B, the projections resiliently interlock with the receptacles to secure the garment 20 on a wearer.

In the illustrated embodiments shown in FIGS. 4A and 6A, the depth of the recesses in the gripping means 50 are shown as dimension E while the height of the projections of the target means 52 are shown as dimension F. From the above discussion, it is apparent that in the embodiment of FIG. 6A the depth of the recesses and the height of the projections are one and the same. The depth and height dimensions E and F of FIG. 4A are illustrated as being substantially equal, although variations of these dimensions from one another are possible as long as the projections and recesses have an adequate sidewall interengagement to maintain interconnection.

Figure 7:
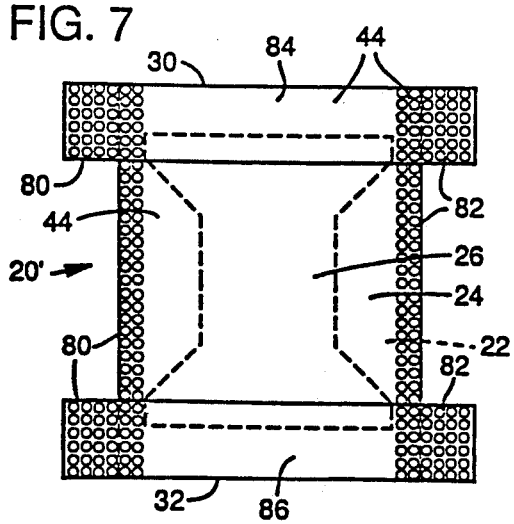
FIGS. 7 and 8 illustrate one method of manufacturing one form of a disposable absorbent garment of the present invention, with FIG. 7 illustrating the garment prior to the final cutting operation, and FIG. 8 showing the garment after cutting of the side contours.
Figure 8:
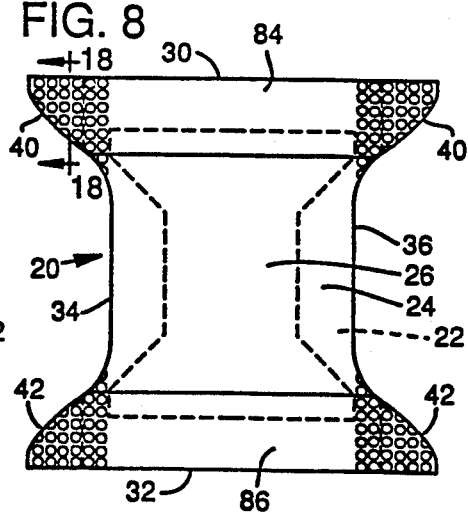

FIGS. 7 and 8 illustrate a method of manufacturing the disposable absorbent garment having the closure system 48 of the present invention. In FIG. 7, the garment 20' is shown prior to the final cutting, such as by a laser or waterknife, which results in the hourglass shape of garment 20 as illustrated in FIGS. 1 and 8. Such a method of manufacture is described in U.S. Pat. No. 4,726,807, issued to the coinventors of this present invention, and previously incorporated by reference into this detailed description.

Referring to FIG. 7, two strips of connectors 80 and 82 lie along each side of the unfinished garment 20'. The connectors may be preformed on strips which are then attached to the garment 20' in the locations shown either by adhesive means, heat bonding, sonic bonding or other suitable attachment means. Alternatively, the connectors may be formed in the regions 80 and 82 by deformation of the outer layer 22 and the inner layer 24, that is to the extent that the inner layer 24 extends into the regions. Thus, the gripping means 50 and target means 52 may be located at least partially in the outer boundary 44 where the inner and outer layers 24 and 22 are joined. A reinforcing strip of a thermoplastic material, such as 5 mil (0.005 inches) thick polyester, may be bonded to the regions 80, 82 to enhance the strength of the gripping means 50 and target means 52. Alternatively, such a reinforcing layer may be applied only in the area of the waste extensions 40, 42 as shown in FIG. 1.

Referring to FIGS. 7 and 8, such reinforcement may alternatively be provided by first and second moisture barriers 84 and 86 of a moisture impervious material, which extend along the respective first and second waist edges 30, 32. The illustrated moisture barriers 84 and 86 include a moisture barrier flap which extends over the inner layer 24 and over the ends of the absorbent core 26 which lie adjacent and substantially parallel to the first and second waist edges 30, 32.

The moisture barrier flaps 84 and 86 may also each extend over their respective first and second waist edges 30 and 32 to overlie a portion of the outer layer 22. In this manner, a moistureproof barrier is formed along each waist edge. This waist edge seal prevents leakage by capillary action from the core 26 of the diaper along the inner layer 24 and onto the outer garments of a wearer along the waist. The moisture barrier flaps 84, 86 may be attached to the inner and outer layers 24, 22, such as by adhesive means. Each moisture barrier 84, 86 extends along the length of the adjacent waist edge 30, 32 substantially between each of the two opposed side margins 40, 42, respectively. If the moisture barriers are also required to enhance the strength of the gripping means 50 and target means 52, the respective moisture barriers 84 and 86 will extend to include the waist extensions 40, 42, as illustrated in FIG. 18. Note, that if the line 18—18 of FIG. 8 had been drawn a distance of two columns of connectors to the right of that shown in FIG. 8, FIG. 18 would also illustrate the inner layer 24, lying adjacent to the left of the outer layer 22.

In forming the projections and receptacles by deformation, the gripping means 50 and target means 52 may be of an embossable material, and the first and second connectors 54, 56 may be embossed thereon. Such embossing may occur in any conventional manner, such as by stamping or by vacuum drawing of the sheet material into a die. A flat die may be used, or alternatively, the unfinished garment 20' may be propelled over a wheeled die, that is a wheel having the appropriately sized and spaced projection or receptacle configurations formed in the outer periphery of the wheel.

As mentioned above, the connectors of the gripping means 50 and target means 52 may be embossed upon the garment 20 or bonded thereto. Such bonding of the target means to the outer surface 22 of garment 20 may be by adhesive, ultrasonic means, heat fusion means or any other suitable bonding means. In FIG. 9, the garment 20 has target means 52 adhesively attached along the front waist edge 30 comprising a pair of targets 52a and 52b. The targets 52a and 52b are located along the respective opposed side margins 36 and 34.

In FIG. 10, the target means 52 are also illustrated as a pair of targets 52c and 52d, bonded to the outer sheet 22 along the front waist edge 30. However, the embodiment of FIG. 10 differs from FIG. 9 in that each of the pair of targets 52c and 52d are positioned to extend slightly beyond the opposed respective side margins 36, 34.

The gripping means 50 of FIG. 9 are comprised of two tabs 50a and 50b which extend outwardly from the respective side margins 36 and 34 along the second waist edge 32. The gripping tabs 50a and 50b are bonded, such as by adhesive attachment means, to the inner sheet 24 of garment 20. Alternatively, the gripping tabs 50a and 50b may be sandwiched between the inner and outer sheets 24, 22, or they may be sandwiched between a moisture barrier 86 (shown in FIG. 8) and either sheet 22 or 24, or they may be bonded directly to the outer surface of the moisture barrier strip 86.

The gripping means 50 in the FIG. 10 embodiment comprises gripping tabs 50c and 50d which have a location similar to that of the gripping means 50 of FIG. 9. However, the embodiment of FIG. 10 differs from that of FIG. 9 in that a portion of each of the gripping tabs 50c and 50d is bonded, such as by adhesive attachment means, to the outer layer 22.

FIG. 11 illustrates gripping means 50 as a continuous gripping strip 50e which extends along the length of the second waist edge 32 and extends beyond each of the opposed side margins 34 and 36. The target means 52 of the FIG. 11 embodiment is comprised of a continuous target strip 52e which extends along the length of the first waist edge 30 substantially between each of the opposed Side margins 36 and 34.

The target strip 52e and the gripping strip 50e of FIG. 11 may each be of a moisture impervious material and may have a flap which extends over the respective waist edges 30 and 32 and on to a portion of the inner layer 24. In this manner, the target strip 52e would form a first moisture barrier strip and the gripping strip 50e would form a second moisture barrier strip, similar to the moisture barrier strips 84 and 86 of FIG. 8. As illustrated in FIG. 11, the strip 50e extends beyond each of the opposed side margins to form respective left and right tabs, with the left tab preferably being adjacent side margin 34 and the right tab preferably being adjacent side margin 36.

In addition to illustrating the various positions and embodiments of the gripping means and target means, FIGS. 9, 10 and 11, along with FIGS. 12A and 12B, illustrate an additional embodiment of the closure system 48 of the present invention. These embodiments illustrate the gripping means 50 as a strip having a first thickness G as shown in FIG. 12A. Each of the first connectors 54 of the gripping means 50 has a throat 60 which extends through the thickness G of the gripping means strip. The throat 60 has a first cross-sectional dimension H which is substantially constant through the entire thickness G of the gripping strip.

The target means 52 include second connectors 56 each comprising a projection having a distal end portion 70 and a middle portion 72 spaced inwardly from the distal end portion. The distal end portion 70 has a second cross-sectional dimension J (the capital letters "I", "O" and "S" are not used to label dimensions within this description) which is slightly larger than the first cross-sectional dimension H of the first connector throat 60. The middle portion 72 has a cross-sectional dimension K which is substantially equal to the first cross-sectional dimension H of throat 60. The length of the middle portion 72 labeled as L is substantially equal to the first thickness G of the gripping strip. Thus, when the target means 50 and the gripping means 52 are coupled together, the distal end portion 70 of the target means is positioned beyond the throat portion 60 of the gripping means 50, as shown in FIG. 12B. In this manner, the garment 20 is releasably secured upon a wearer of the garment.

Once again, while the first and second connectors 54, 56 in FIGS. 9, 10, 11, 12A and 12B are illustrated as having a substantially circular cross section, other cross-sectional shapes would also be suitable. For example, squares, rectangles, ovals, elongated slots, and so forth. Any of these shapes, or combinations thereof, would be suitable provided that the throat 60 of the gripping means 50 was sized to surround and releasably engage the projecting second connectors 56.

FIGS. 9, 10 and 11 illustrate three rows of second connectors 56 lying substantially parallel to the first edge 30. The first connectors 54 are arranged in at least two rows, with each row substantially parallel to the second waist edge 32. As illustrated in FIG. 9, the first connector rows are spaced a first distance M apart, and the first connectors within each row are spaced a second distance N apart. The second connectors 56 are arranged in at least two rows, with each row being substantially parallel to the first waist edge 30. The second connector rows are spaced the first distance M apart and the second connectors within each row are spaced the second distance N apart. In this manner, the first and second connectors 54, 56 of the gripping means and target means 50, 52 are easily aligned for interconnection. Additional or fewer rows of connectors, as well as rows located other than parallel to the waist edges, would also be suitable.

FIG. 9 illustrates gripping means 50 comprising two rows of first connectors, substantially parallel to the second waist edge 32. The gripping tabs 50a and 50b are of a width which allows placement of the two rows of first connectors 54 over one of either the two adjacent rows of second connectors 56 which are proximate to the first waist edge 30, or the two adjacent rows of second connectors 56 that are distal to the first waist edge 30. This allows adjustment of the garment size in an axial direction, that is lengthening or shortening the garment through the crotch region. A similar effect can be accomplished by placement of the gripping connectors 50c and 50d of FIG. 10 to interengaging only one or two rows of the target means 52c and 52d.

The embodiment of FIG. 11 provides in addition to the axial sizing flexibility of FIGS. 9 and 10, the choice of a greater variety of waist sizes. For example, the gripping means 50e could be connected along any of the second connectors 56 of the target strip 52e. To provide for a large waist size fastener, system 48 is connected near the side margins 34, 36, and for smaller waist sizes, the fastener system is connected at positions located substantially inward from the boundaries of the side margins. Such adjustments are also possible using the embodiments illustrated in FIGS. 1 through 8. Additionally, the fastener systems illustrated in FIGS. 3 through 6 could also extend along the length of the waist edges as shown in FIG. 11. However, having only the target means 52 extend along the waist edge 30 may be a more preferred embodiment.

FIGS. 13 through 17 illustrate a disposable absorbent garment having a closure system 48 wherein the first and second connectors 54, 56 comprise interlocking ridges and grooves. FIGS. 13 and 17 illustrate the gripping means 50 and target means 52 as being bonded to the outer surface 22 of the garment 20, such as by adhesive means or any other suitable bonding means. The gripping means 50 and target means 52 of FIGS. 13 and 17 could also be extended across their respective adjacent waist portions 32, 30 in the manner illustrated by FIG. 11.

The interlocking ridges and grooves of the gripping means and target means illustrated in FIG. 13 are particularly well suited to formation by extrusion means, such as through an extrusion die. Subsequent to extrusion, the gripping means and target means are cut into strips of the desired width, that is the dimension which is perpendicular to the first and second waist edges 30, 32 of FIG. 13. After this, the strips are bonded at the locations shown.

Regarding the embodiment of FIG. 16, the target means 52 and the gripping means 50 may each be of an embossable material. In this embodiment, the plurality of interlocking ridges and grooves are shown embossed on the respective side waist extensions 42 and 40. The FIG. 16 embodiment could be manufactured in the manner discussed in connection with FIGS. 7 and 8 above. Additionally, moisture barrier strips, such as 84 and 86 (see FIG. 8) may also be included in this embodiment, as well as those of FIGS. 13 and 17.

To more particularly describe the orientation of the ridges and grooves relative to the illustrated hourglass shape, a longitudinal axis 90 is shown in FIGS. 13, 16 and 17. The longitudinal axis 90 is substantially perpendicular to the first and second waist edges 30, 32 and substantially centered between the opposed side margins 34, 36.

Turning specifically now to the embodiment of FIGS. 13, 14A and 14B, the gripping means 50 comprises a pair of gripping strips 50f and 50g, each having opposed first and second sides 92 and 94. As shown in FIG. 13, a portion of the first side 92 of each gripping strip is bonded to the garment outer layer 22. Alternatively, a portion of the second side 94 of each gripping strip may be bonded to the inner layer 24, or the gripping strips may be sandwiched between the inner and outer layers and/or a moisture barrier strip 86 (see FIG. 8) and bonded thereto. The illustrated target means 52 comprises a pair of target strips 52f and 52g, each having opposed first and second sides 96, 98. As shown in FIG. 13, at least a portion of the second side 98 of each target strip is bonded to the outer layer 22 of the garment 20.

As illustrated in FIGS. 14A and 14B, and with reference to FIG. 13, each of the gripping means first connectors 54 comprises a groove 100 defined by two opposed upright side ribs 102 and 104 extending outwardly from the first side 92 of each gripping strip. Each of the target means second connectors 56 comprises a ridge 106 projecting outwardly from the first side 96 of each target strip. The grooves 100 and ridges 106 are aligned respectively substantially parallel to one another. The plurality of grooves 100 are interlockable with the plurality of ridges 106. In an alternate embodiment (not shown), each of the gripping means first connectors 54 may be an interlockable ridge 100, and each of the target means second connectors 56 may be an interlockable groove 106. Another alternate embodiment of interlocking grooves 108 and ridges 110 is shown in FIGS. 15A and 15B, with a plurality of adjacent ridges 110 and grooves 108 being integrally formed on both the gripping means 50 and the target means 52. Any of these embodiments are suitable for use on the garments 20 of FIGS. 13 and 16.

In the disconnected fastener embodiments of FIGS. 14A and 15A, the grooves 100, 108 form the receptacles, with each including an entrance 58 defining a throat 60 which has a first cross-sectional dimension P. In FIGS. 14A and 14B, each receptacle groove 100 includes a bottom surface 62, with the opposed upright side ribs 102 and 104 each forming one of two opposed concave interior sidewalls 64 and 66 which extend between the entrance 58 and the bottom surface 62. In FIGS. 15A and 15B, each receptacle groove 108 of FIGS. 15A and 15B includes a bottom surface 62 and two opposed sidewalls 64 and 66 which are also the sidewalls defining the bordering adjacent grooves 110. The opposed sidewalls 64, 66 of FIGS. 14A and 15A preferably taper outwardly from the entrance 58, to define an interwall cross-sectional dimension Q which is greater than the throat first cross-sectional dimension P.

In FIGS. 14A and 15A, each of the respective projecting ridges 106, 110 includes a distal end portion 70 and a middle portion 72 which is spaced inwardly from the distal end portion 70. The distal end portion 70 has a cross-sectional dimension R which is greater than the throat first cross-sectional dimension P, and substantially equal to the interwall cross-sectional dimension Q of the receptacle. The projection middle portion 72 has a cross-sectional dimension T which is substantially equal to the throat first cross-sectional dimension P. These cross-sectional dimensions, P, Q, R and T are given by way of illustration, and may vary slightly as long as interconnection is maintained during wearer activity.

Thus, upon interengagement of the receptacle grooves 100, 108 with the respective projecting ridges 106, 110 of FIGS. 14B and 15B, the distal end portion cross-sectional dimension R of each ridge substantially coincides with the interwall cross-sectional dimension Q of an interengaged groove. The projection middle portion 72 cross-sectional dimension T also substantially coincides with an interengaged throat 60 first cross-sectional dimension P. In this manner, a ridge distal end portion 70 is interlocked between the opposed walls 64, 66 of a groove by the groove throat 60 resiliently gripping the middle portion 72 of the ridge.

The grooves and ridges of FIGS. 13 and 16 are illustrated as aligned parallel to the garment longitudinal axis 90. This parallel alignment forms a connection which is strong in sheer strength, and not likely to be pulled apart during activity of the wearer. During such activity, such as if the wearer bends over at the waist, the waist region of the garment adjacent edges 30 and 32, including the closure system 48, is subject to expansive forces. If such ridges and grooves were aligned parallel to the waist edges 30 and 32, they may axially slip out of interengagement. Thus the orientation of the grooves and ridges perpendicular to the waist edges is preferred. However, the ridges and grooves may also be placed at some angle to the longitudinal axis 90, such as at forty-five degrees. In this configuration, the grooves and ridges on the gripping means 50 adjacent one side margin, for example 34, must be substantially parallel to the ridges or grooves on the gripping means 52 which is also located adjacent side margin 34. The same substantially parallel requirement would also apply to the angle of the ridges and grooves of the gripping means and target means adjacent side 36.

Thus, alternate embodiments having the parallel grooves and ridges aligned at angles other than parallel to the longitudinal axis 90 are also possible. Additionally, FIG. 17 illustrates gripping means 50 comprising a pair of gripping strips 50$h$ and 50$j$ each having first connectors 54 comprising a plurality of segmented ridges or ridge segments 112. The ridge segments 112 are each aligned end-to-end in rows, with adjacent segments within a row being separated by a small space 114. The garment 20 also includes target means 52 comprising a pair of targets 52$h$ and 52$j$ located along the respective side margins 36 and 34. Each of the targets comprises a plurality of grooves 116 lying in a substantially concentric arcuate pattern. The arcuate grooves 116 are convex substantially toward the center of the garment or that is, toward the crotch portion 38. In this manner, the ridge segments 112 of the gripping means 52 interengage portions of the arcuate grooves 116 on the target means 50.

In a typical use of the garment 20, such a diaper for a baby, the baby is typically diapered while lying on his or her back. In the most convenient method of fitting the diaper, the second waist edge 32 is placed under the back of the baby, with the inner layer 24 toward the baby. The diaper is adjusted so that the second waist edge 32 is approximately under the baby's back at the waist and the baby's bottom is set down upon the diaper to hold it in place. The front waist edge 30 and crotch portion 38 are brought upward between the baby's legs to the point where the first waist edge 30 is approximately over the baby's waist at the front. The gripping means 50 are pulled from the back and around each side of the baby to overlap and interengage the target means 52. Interengagement is accomplished by pressing downwardly on the gripping means, that is in a direction toward and substantially perpendicular to the outer sheet 22 lying under the target means 52. Removal of the diaper, such as for checking or readjustment, is accomplished by pulling upwardly on the gripping means 50, that is in a direction away from and substantially perpendicular to the outer sheet 22 as it lies under the target means 52.

Since no adhesives are used, the gripping means 50 and target means 52 of the mechanical fastener or closure system 48 are not vulnerable to degradation by contamination from the various ointments and powders which may be applied to a baby's bottom. Nor is the closure system of the present invention subject to contamination from various foreign textile fibers, such as a changing table cover or the baby's outer clothing, as are adhesive and VELCRO fasteners. Additionally, the orientation of both the interlocking throats and projections being substantially perpendicular to the outer surface 22 provides a closure system 48 that is strong when subjected to sheer forces caused by expansion of the wearer's waist during activity. This orientation also provides a closure system that is relatively easy to interconnect and disconnect by respective downward and upward motions, that is, toward and away from the outer sheet 22 in a direction substantially perpendicular to the outer sheet 22 under the region of the target means 52.

Having illustrated and described the principles of our invention with respect to several preferred embodiments, it should be apparent to those skilled in the art that our invention may be modified in arrangement and detail without departing from such principles. We claim all such modifications falling within the scope and spirit of the following claims.

We claim:

1. A disposable absorbent garment comprising:
   a liquid impervious outer layer;
   a nonwoven liquid pervious inner layer;
   an absorbent layer sandwiched and encased between the inner and outer layers, the sandwiched layers having opposed front and back laterally extending waist edges with a crotch region therebetween, and two opposed side margins extending generally in an axial direction between the front and back waist edges, the front and back waist edges for extending along the respective front and back waist edges for extending along the respective front and back waist portions of a wearer;
   resiliently deformable gripping connectors extending from each of the side margins along the back waist edge, the gripping connectors comprising a plurality of projections and recesses formed by deformations of both the inner and outer layers; and
   target connectors along connectors along the front waist edge for engaging and securing the gripping connectors, the target connectors comprising a plurality of projections and recesses formed by deformation of both the inner and outer layers for engaging the gripping connectors, said target connectors adapted each to receive at least one of said gripping connectors by pressing the gripping connectors substantially perpendicularly toward the target connectors form either the inner layer or the outer layer, said gripping and target connectors being sized such that upon interengagement, at least one of said gripping and target connectors are deformed and said gripping and target connectors resiliently grip one another to maintain interconnection.

2. A disposable garment according to claim 1, wherein;
   the garment also comprises a moisture impervious material extending along the length of the front waist edge substantially between each of the opposed side markings; and
   at least some of the plurality of projections and recesses of the target connectors are also integrally formed from the moisture impervious material.

3. A disposable absorbent garment according to claim 2 wherein the moisture impervious material comprises a moisture barrier flap which extends from the outer surface over the front waist edge and over the inner layer, the flap being attached to the inner layer to form a moisture proof barrier along the first waist edge.

4. A disposable absorbent garment comprising:
   a liquid impervious luster layer;
   a nonwoven liquid pervious inner layer;
   an absorbent layer sandwiched and encased between the inner and outer layers, the sandwich layers having opposed front and back laterally extending waist edges with a crotch region therebetween, and two opposed side margins extending generally in an axial direction between the front and back waist edges, the front and back waist edges for extending along the respective front and back waist portions of a wearer;
   resiliently deformable gripping connectors extending from each of the side margins along the back waist edge, the gripping connectors comprising a plurality of projections and recesses formed by deformation of both the inner and outer layers; and
   target connectors along the front waist edge for engaging and securing the gripping connectors, the target connectors comprising a plurality of projections and recesses formed by deformations of both the inner and outer layers or engaging the gripping connectors, said target connectors adapted each to receive at least one of said gripping connectors by pressing the gripping connectors substantially perpendicularly toward the target connectors from either the inner layer or the luster layer, said gripping and target connectors being sized such that upon interengagement, at least one of said gripping and target connectors are deformed and said gripping and target connectors resiliently rip one another to maintain interconnection;
   wherein the outer impervious layer extends outwardly from each of the opposed side margins along the front and back waist edges to form a pair of front waist extensions extending from the front waist edge and a pair of back waist extensions extending from the back waist edge;
   wherein the gripping connectors are embossed on each of the back waist extensions; and
   wherein the target connectors are embossed on each of the front waist extensions.

5. A disposable garment according to claim 1 wherein the target connectors comprises a pair of targets, one of each of the pair of targets located along one of each of the opposed side margins.

6. A disposable absorbent a garment according to claim 1 wherein the sandwiched layers generally have an hourglass shape, with the top and bottom of the hourglass shape forming the front an back waist portions of the garment, and with the opposed sides of the hourglass shape forming the opposed side margins, and with a crotch portion of the garment central to the hourglass shape having a narrower width than the waist portions.

7. A disposable garment according to claim 1, wherein the gripping and target connectors are arranged for interengagement in plural axially and laterally shifted positions so as to allow lateral adjustment of the garment size to fit varying waist sizes and to allow adjustment of the garment size in the axial direction for lengthening and shortening the garment through the crotch region.

8. A disposable garment according to claim 2, wherein:
   the garment also comprises a second moisture imperious material extending along the length of the back waist edge substantially between each of the opposed side margins; and
   at least some of the plurality of projections and recesses of the gripping connectors are also integrally formed from the second moisture impervious material.

9. A disposable garment according to claim 1, wherein:
   the gripping connector projections comprise a plurality of ridges, and the gripping connector recesses comprise a plurality of grooves; and the target connector projections comprise a plurality of ridges, and the target connector recesses comprise a plurality of grooves.

10. A disposable garment according to claim 9, wherein the ridges and grooves of both the gripping connectors and the target connectors extend generally in the axial direction.

11. A disposable garment according to claim 9, wherein:

the outer impervious layer extends outwardly from each of the opposed side margins along the front and back waist edges to form a pair of front waist extensions, extending from h front waist edge, and a pair of back waist extensions, extending from the back waist edge;

wherein the gripping connectors are embossed on each of the back waist extensions; and wherein the target connectors are embossed on each of the front waist extensions.

* * * * *

UNITED STATES PATENT AND TRADEMARK OFFICE
CERTIFICATE OF CORRECTION

PATENT NO. : 5,324,279

DATED : June 28, 1994

INVENTOR(S) : Lancaster et al.

It is certified that error appears in the above-identified patent and that said Letters Patent is hereby corrected as shown below:

Column 4, line 13, "textile fibbers" should be --textile fibers--;

Column 12, line 37, "Side" should be --side--.

Column 17, line 28, "connectors along connectors along" should be --connectors along--.

Column 17, lines 19-20, "waist edges for extending the respective front and back waist portions" should be --waist portions--;

Column 17, line 37, "form" should be --from--;
    Column 17, line 49, "markings;" should be --margins;--;
    Column 17, line 60, "luster" should be --outer--;
    Column 17, line 63, "sandwich" should be --sandwiched--;
    Column 18, line 12, "or" should be --for--;
    Column 18, line 17, "luster" should be --outer--;
    Column 18, line 21, "rip" should be --grip--;
    Column 18, line 34, "comprises" should be --comprise--;
    Column 18, line 37, "a" should be deleted;
    Column 18, line 40, "an" should be --and--;
    Column 20, line 4, "h" should be --the--.

UNITED STATES PATENT AND TRADEMARK OFFICE
CERTIFICATE OF CORRECTION

PATENT NO. : 5,324,279
DATED : June 28, 1994
INVENTOR(S) : Lancaster et al.

It is certified that error appears in the above-indentified patent and that said Letters Patent is hereby corrected as shown below:

Column 20, line 4, "h" should be --the--.

Signed and Sealed this

Thirteenth Day of December, 1994

Attest:

BRUCE LEHMAN

Attesting Officer     Commissioner of Patents and Trademarks